United States Patent [19]
Outtrup et al.

[11] Patent Number: 5,770,424
[45] Date of Patent: Jun. 23, 1998

[54] DNA CONSTRUCTS AND METHODS OF PRODUCING XYLANOLYTIC ENZYMES

[75] Inventors: Helle Outtrup, Bellerup; Claus Dambmann, Søborg; Arne Agerlin Olsen, Virum; Henrik Bisgård-Frantzen, Lyngby; Martin Schülein; Per Linaa Jorgensen, both of Copenhagen, all of Denmark

[73] Assignee: NovoNordisk A/S, Bagsvaerd, Denmark

[21] Appl. No.: 698,978

[22] Filed: Aug. 16, 1996

Related U.S. Application Data

[63] Continuation-in-part of Ser. No. 470,398, Jun. 6, 1996, which is a continuation of Ser. No. 343,600, filed as PCT/DK93/00218 Jul. 2, 1993, abandoned.

[51] Int. Cl.$^6$ .............................. C12N 9/24; C12N 1/20; C12N 15/00; C07H 21/04
[52] U.S. Cl. .................. 435/200; 435/200; 435/252.3; 435/252.31; 435/320.1; 536/23.2
[58] Field of Search ................................. 435/200, 320.1, 435/252.3, 252.31, 25.3; 536/23.2

[56] References Cited

FOREIGN PATENT DOCUMENTS

| 25086/95 | 2/1996 | Australia | 435/200 |
|---|---|---|---|
| 95/18219 | 6/1995 | WIPO | 435/200 |

OTHER PUBLICATIONS

Yu et al. (1990) Nucleotide sequence and analysis of a xylanase gene (xynS) from alkali–tolerant Bacillus sp. YA–14 and comparison with other xylanases. Genbank submission Acc No.: X59059, Dec. 4, 1990.

Na et al. (1990) Recombinant plasmid DNA containing xylanase and betat–xylosidase gene of Bacillus sp. YA–14, Sanop Misaengmul Hakhoechi 18(2): 195–198, Jan. 1990.

Fukusaki et al. (1984) The complete nucleotide sequence of the xylanase gene (xynA) of *Bacillus pumilus,* FEBS Letters 171(2): 197–201, Jun. 1984.

Zappe et al. (1990) Nucleotide sequence of a *Clostridium acetobutylicum* P262 xylanase gene (xynB), Nucleic Acids Research 18(8): 2179, Jun. 1990.

Ko et al. (1992) Site–directed mutagenesis at aspartate and glutamate residues of xylanase from *Bacillus pumilus,* Biochem. J. 288: 117–121, Nov. 15, 1992.

Sakka et al. (1993) Nucleotide Sequence of the *Clostridium stercorarium* xynA Gene Encoding Xylanase A: Identification of Catalytic and Cellulose Binding Domains, Biosci. Biotech. Biochem. 57 (2): 273–277. Feb. 1993.

Rudinger, J. (1976) Characteristics of the amino acids as components of a peptide hormone sequence, In Peptide Hormones, Ed. J. A. Parsons, pp. 1–7, Jun. 1976.

Mierendorf et al. (1987) Gene Isolation by Screening lambda gt 11 Libraries with Antibodies, In Guide to Molecular Cloning Techniques, Eds. S. L. Berger and A. R. Kimmel. pp. 458–469, Jan. 1987.

*Primary Examiner*—Robert A. Wax
*Assistant Examiner*—Einar Stole
*Attorney, Agent, or Firm*—Steve T. Zelson, Esq.; Valeta Gregg, Esq.

[57] ABSTRACT

The present invention is directed to isolated nucleic acid constructs comprising a nucleic acid sequence encoding xylanolytic enzymes derived from a strain of *Bacillus agaradherens,* recombinant vectors and host cells comprising such constructs, and methods for obtaining xylanolytic enzymes.

12 Claims, 1 Drawing Sheet

DNA CONSTRUCTS AND METHODS OF PRODUCING XYLANOLYTIC ENZYMES

CROSS-REFERENCE TO RELATED APPLICATIONS

This application is a continuation-in-part of U.S. patent application Ser. No. 08/470,398, filed Jun. 6, 1996, which is a continuation of U.S. patent application Ser. No. 08/343,600, filed Nov. 30, 1994, now abandoned, which is a 35 U.S.C. 371 national application of PCT/DK93/00218 filed 2 Jul. 1993, all of which applications are specifically incorporated herein by reference and to which is claimed priority under 35 U.S.C. § 120.

TECHNICAL FIELD

The present invention is directed to isolated nucleic acid constructs comprising a nucleic acid sequence encoding xylanolytic enzymes derived from a strain of *Bacillus agaradherens*, recombinant expression vectors and host cells comprising such constructs, and methods for obtaining xylanolytic enzymes.

BACKGROUND OF THE INVENTION

International Patent Application WO 94/01532 describes a new species of alkalophilic Bacillus, with the proposed name Bacillus sp. AC13, as well as proteases, xylanases and cellulases obtainable therefrom. WO 94/01532 also describes methods for the production of these enzymes by cultivation of a strain of Bacillus sp. AC13. However, WO 94/01532 does not describe nucleic acid constructs comprising a nucleic acid sequence encoding xylanolytic enzymes derived from a strain Bacillus sp. AC13, or methods of producing these xylanolytic enzymes by recombinant DNA technology.

The same new species as described in WO 94/01532 has been described by Nielsen et al. [Nielsen P, Fritze D and Priest F G, *Microbiology* 1995 141 1745–1761], now with the proposed name *Bacillus agaradherens*, which most probably is going to be the established name for this new species. Nielsen et al., however, do not describe nucleic acid constructs comprising a nucleic acid sequence encoding xylanolytic enzymes derived from a strain *Bacillus agaradherens*, or methods of producing these xylanolytic enzymes by recombinant DNA technology.

SUMMARY OF THE INVENTION

According to the present invention, the inventors have now isolated and characterized a DNA sequence derived from *Bacillus agaradherens* encoding a xylanolytic enzyme, thereby making it possible to prepare a mono-component enzyme preparation.

Accordingly, in a first aspect, the invention provides a DNA construct comprising a DNA sequence encoding a xylanolytic enzyme, which DNA sequence,
 (a) comprises the DNA sequence presented as SEQ ID NO: 1; or
 (b) comprises a sequence analogue to the DNA sequence presented as SEQ ID NO: 1, which analogue sequence,
  (i) hybridizes with the DNA sequence presented as SEQ ID NO: 1; or
  (ii) encodes a xylanolytic enzyme which is at least 70% homologous with the xylanolytic enzyme encoded by a DNA sequence comprising the DNA sequence presented as SEQ ID NO: 1; or
  (iii) encodes a xylanolytic enzyme which is immunologically reactive with an antibody raised against a purified xylanase derived from a strain of *Bacillus agaradherens*.

In further aspects the invention provides an expression vector harbouring the DNA construct of the invention, a cell comprising the DNA construct or expression vector of the invention, as well as a method of producing a xylanolytic enzyme, which method comprises culturing the cell of the invention under conditions permitting the production of the enzyme, and recovering the enzyme from the culture.

In a still further aspect the invention provides a xylanolytic enzyme, which enzyme,
 (a) is encoded by a DNA construct of the invention; or
 (b) is produced by the method of the invention; and/or
 (c) is immunologically reactive with an antibody raised against a purified xylanolytic enzyme derived from the strain *Bacillus agaradherens*, NCIMB 40482.

BRIEF DESCRIPTION OF THE DRAWINGS

The present invention is further illustrated by reference to the accompanying drawing, in which.

DETAILED DISCLOSURE OF THE INVENTION

DNA Constructs

Figure 1:
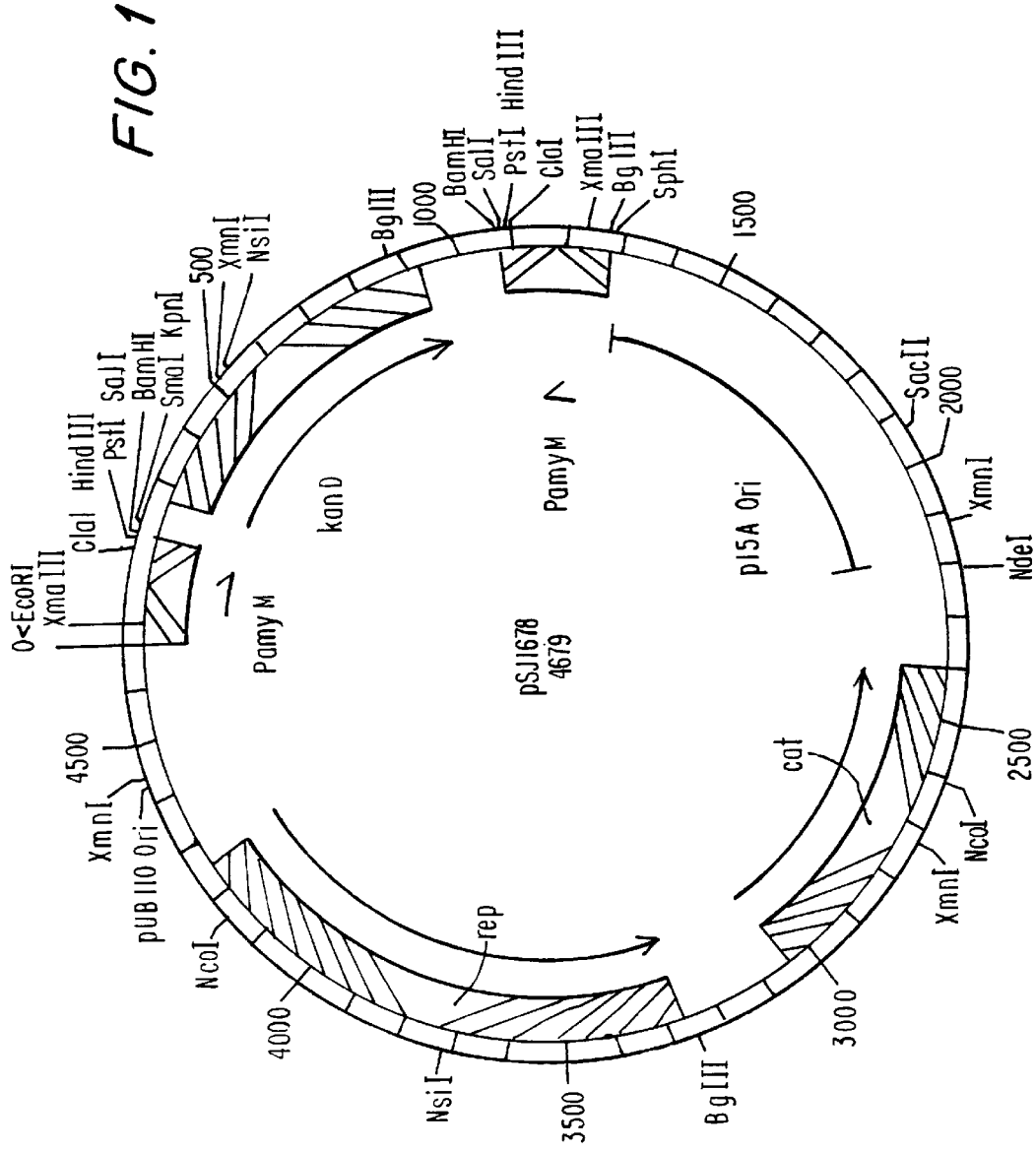
FIG. 1 shows a plasmid map of the cloning vector pSJ1678 used for cloning the XynA gene from *Bacillus agaradherens*, NCIMB 40482.

The present invention provides a DNA construct comprising a DNA sequence encoding a xylanolytic enzyme, which DNA sequence,
 (a) comprises the DNA sequence presented as SEQ ID NO: 1; or
 (b) comprises a sequence analogue to the DNA sequence presented as SEQ ID NO: 1, which analogue sequence,
  (i) hybridizes with the DNA sequence presented as SEQ ID NO: 1; or
  (ii) encodes a xylanolytic enzyme which is at least 70% homologous with the xylanolytic enzyme encoded by a DNA sequence comprising the DNA sequence presented as SEQ ID NO: 1; or
  (iii) encodes a xylanolytic enzyme which is immunologically reactive with an antibody raised against a purified xylanase derived from the strain *Bacillus agaradherens*, NCIMB 40482.

As defined herein the term "DNA construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding a xylanolytic enzyme of interest. The construct may optionally contain other nucleic acid segments.

The DNA construct of the invention preferably is of microbial origin, preferably derived strain of the new species *Bacillus agaradherens*.

The DNA construct of the invention encoding the xylanolytic enzyme may suitably be of genomic or cDNA origin, for instance obtained by preparing a genomic or cDNA library and screening for DNA sequences coding for all or part of the xylanolytic enzyme by hybridization using synthetic oligonucleotide probes in accordance with standard techniques (cf. e.g. Sambrook et al., *Molecular Cloning. A Laboratory Manual*, Cold Spring Harbor, N.Y., 1989).

The nucleic acid construct of the invention encoding the xylanolytic may also be prepared synthetically by established standard methods, e.g. the phosphoamidite method described by Beaucage and Caruthers, *Tetrahedron Letters* 1981 22 1859–1869, or the method described by Matthes et al., *EMBO Journal* 1984 3 801–805. According to the phosphoamidite method, oligonucleotides are synthesized, e.g. in an automatic DNA synthesizer, purified, annealed, ligated and cloned in suitable vectors.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct may also be prepared by polymerase chain reaction using specific primers, for instance as described in U.S. Pat. No. 4,683,202 or by Saiki et al., *Science* 1988 239 487–491.

In a currently preferred embodiment, the nucleic acid construct of the invention comprises the DNA sequence shown in SEQ ID NO: 1, on any subsequence thereof, but which differ from the DNA sequence shown in SEQ ID NO: 1 by virtue of the degeneracy of the genetic code. The invention further encompasses nucleic acid sequences which hybridize to a nucleic acid molecule (either genomic, synthetic or CDNA or RNA) encoding the amino acid sequence shown in SEQ ID NO: 1, or any subsequence thereof, under the conditions described below.

Analogous DNA Sequences

As defined herein, a DNA sequence analogue to the DNA sequence presented as SEQ ID NO: 1 is intended to indicate any DNA sequence encoding a xylanolytic enzyme, which enzyme has one or more of the properties cited under (i)–(iii), above.

The analogous DNA sequence may preferably be isolated from a strain of *Bacillus agaradherens* on the basis of the DNA sequence presented as SEQ ID NO: 1, or any subsequence thereof, e.g. using the procedures described herein, and thus, e.g. be an allelic or species variant of the DNA sequence comprising the DNA sequence presented herein.

Alternatively, the analogous sequence may be constructed on the basis of the DNA sequence presented as SEQ ID NO: 1, or any subsequence thereof, e.g. by introduction of nucleotide substitutions which do not give rise to another amino acid sequence of the xylanolytic enzyme encoded by the DNA sequence, but which corresponds to the codon usage of the host organism intended for production of the enzyme, or by introduction of nucleotide substitutions which may give rise to a different amino acid sequence.

When carrying out nucleotide substitutions, amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine). For a general description of nucleotide substitution, see e.g. Ford et al., *Protein Expression and Purification,* 2 1991 95–107.

It will be apparent to persons skilled in the art that such substitutions can be made outside the regions critical to the function of the molecule and still result in an active xylanolytic enzyme. Amino acids essential to the activity of the xylanase encoded by the DNA construct of the invention, and therefore preferably not subject to substitution, may be identified according to procedures known in the art, such as site-directed mutagenesis or alanine-scanning mutagenesis (cf. e.g. Cunningham and Wells, *Science* 1989 244 1081–1085). In the latter technique mutations are introduced at every residue in the molecule, and the resultant mutant molecules are tested for biological (i.e. proteolytic) activity to identify amino acid residues that are critical to the activity of the molecule. Sites of substrate-enzyme interaction can also be determined by analysis of crystal structure as determined by such techniques as nuclear magnetic resonance analysis, crystallography or photoaffinity labelling (cf. e.g. de Vos et al., *Science* 1992 255 306–312; Smith et al., *J. Mol. Biol.* 1992 224 899–904; Wlodaver et al., FEBS Lett. 1992 309 59–64).

It will be understood that the DNA sequence presented as SEQ ID NO: 1, or any subsequence thereof, may be used as probes for isolating the entire DNA sequence encoding the xylanolytic enzyme, e.g. the DNA sequence presented as SEQ ID NO: 1.

The hybridization referred to in (i) above is intended to indicate that the analogous DNA sequence hybridizes to the DNA sequence encoding the xylanolytic enzyme under certain specified conditions which are described in detail in the Materials and Methods section below. The test for hybridization preferably is carried out under the conditions defined for low to medium stringency. In a more preferred embodiment, the test for hybridization preferably is carried out under the conditions defined for high stringency.

Normally, the analogous DNA sequence is highly homologous to the DNA sequence, such as at least 70% homologous to the DNA sequence presented as SEQ ID NO: 1 encoding the xylanolytic enzyme of the invention, preferably at least 75%, at least 80%, at least 85%, at least 90% or even at least 95% homologous to said DNA sequence.

The degree of homology referred to in (ii) above is determined as the degree of identity between the two sequences indicating a derivation of the first sequence from the second. The homology may suitably be determined by means of computer programs known in the art, e.g. comparing 50 bp contiguous sequences. In a preferred embodiment homology may be determined using the Clustal method with PAM250 residue weight table, which software is available from LaserGene.

Typically, the xylanolytic enzyme encoded by an analogous DNA sequence exhibits a degree of homology of at least 70% such as at least 75%, at least 80%, at least 85%, at least 90% or even at least 95% with the enzyme encoded by a DNA construct comprising the DNA sequence presented as SEQ ID NO: 1.

The term "derived from" in connection with property (iii) above is intended not only to indicate a xylanolytic enzyme produced by a strain of *Bacillus agaradherens,* but also a xylanolytic enzyme encoded by a DNA sequence isolated from a strain of *Bacillus agaradherens* and produced in a host organism transformed with said DNA sequence. The immunological reactivity may be determined by the method described in the Materials and Methods section below.

The DNA sequence encoding the xylanolytic enzyme may be isolated by conventional methods, which methods may typically involve, cloning, in a suitable vector, a cDNA library from a strain of *Bacillus agaradherens*, e.g. the strain NCIMB 40482, transforming a suitable host cell with said vector, culturing the host cell under conditions suitable to express the desired xylanolytic enzyme encoded by one or more clones in the cDNA library, screening for positive clones by determining any xylanolytic activity of the enzyme produced by such clones, and isolating the DNA encoding the desired xylanolytic enzyme from such clones.

A general method has been disclosed in WO 93/11249, the contents of which are hereby incorporated by reference. A more detailed description of the screening method is given in Example 1 below.

Microbial Sources

The DNA construct of the invention preferably is of microbial origin, preferably derived strain of the new species *Bacillus agaradherens*. As described above, *Bacillus agaradherens* is a new species of alkalophilic Bacilli, which has been disclosed by Nielsen et al., supra.

The type strain of *Bacillus agaradherens* is the strain DSM 8721, which strain strain has been deposited in the open collection of Deutsche Sammlung von Mikroorganismen und Zelikulturen GmbH (DSM), Mascheroder Weg 1b, DE-3300 Braunschweig, Germany.

Another strain representative of the new species *Bacillus agaradherens* has been deposited according to the Budapest Treaty on the International Recognition of the Deposit of Microorganisms for the Purposes of Patent Procedure at National Collections of Industrial and Marine Bacteria, Ltd. (NCIB), 23 St. Machar Drive, GB-Aberdeen AB2 1RY, United Kingdom, on 3 Mar. 1992 and allotted the deposit number NCIB 40482.

Being an International Depository Authority under the Budapest Treaty, NCIB affords permanence of the deposit in accordance with the rules and regulations of said treaty, vide in particular Rule 9. Access to the deposit will be available during the pendency of this patent application to one determined by the Commisioner of the United States Patent and Trademark Office to be entitled thereto under 37 C.F.R. Par. 1.14 and 35 U.S.C. Par. 122. Also, the above mentioned deposit fulfils the requirements of European patent applications relating to micro-organisms according to Rule 28 EPC.

The above mentioned deposits represents substantially pure cultures of an isolated *Bacillus agaradherens*. The deposits are available as required by foreign patent laws in countries wherein counterparts of the subject application, or its progeny are filed. However, it should be understood that the availability of a deposited strain does not constitute a license to practice the subject invention in derogation of patent rights granted by governmental action.

In a more preferred embodiment, the DNA construct of the invention is derived from the strain NCIMB 40482, or the strain DSM 8721, or mutants or variants thereof. The DNA sequence encoding the xylanolytic enzyme may be isolated from these deposits by standard methods, e.g. as described in Example 1.

Further said DNA sequence may be isolated by screening a cDNA library of a strain of *Bacillus agaradherens*, followed by selection for clones expressing the xylanolytic enzyme (e.g. as defined by the ability of the enzyme to hydrolyse 1,3-β-xylosidic linkages in 1,3-βxylans). The appropriate DNA sequence may then be isolated from the clone by standard procedures.

Alternatively, the DNA encoding the xylanolytic enzyme may, in accordance with well-known procedures, conveniently be isolated from DNA from the source in question by use of synthetic oligonucleotide probes prepared on the basis of a DNA sequence disclosed herein. For instance, a suitable oligonucleotide probe may be prepared on the basis of the nucleotide sequences presented as SEQ ID NO: 1, or any suitable subsequence thereof.

Recombinant Expression Vectors

In another aspect, the invention provides a recombinant expression vector comprising the DNA construct of the invention.

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector of the invention, the DNA sequence encoding the xylanolytic enzyme preferably is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the xylanolytic enzyme.

Thus, in the expression vector of the invention, the DNA sequence encoding the xylanolytic enzyme preferably should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the xylanolytic enzyme, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The promoter may be any DNA sequence which shows transcriptional activity in the host cell of choice and may be derived from genes encoding proteins either homologous or heterologous to the host cell.

Examples of suitable promoters for directing the transcription of the DNA encoding the xylanolytic enzyme of the invention in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylanase or xylosidase gene, or by the phage Lambda $P_R$ or $P_L$ promoters or the *E. coli* lac, trp or tac promoters.

Examples of suitable promoters for use in yeast host cells include promoters from yeast glycolytic genes (Hitzeman et al., *J. Biol. Chem.* 255 (1980), 12073–12080; Alber and Kawasaki, *J. Mol. Appl. Gen.* 1 (1982), 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2–4c (Russell et al., *Nature* 304 (1983), 652–654) promoters.

Examples of suitable promoters for use in filamentous fungus host cells are, for instance, the ADH3 promoter (McKnight et al., *The EMBO J.* 4 (1985), 2093–2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

The expression vector of the invention may further comprise a DNA sequence enabling the vector to replicate in the host cell in question. The expression vector may also comprise a selectable marker, e.g. a gene the product of which complements a defect in the host cell, such as the gene coding for dihydrofolate reductase (DHFR) or the *Schizosaccharomyces pombe* TPI gene (described by Russell P R, *Gene* 1985 40 125–130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

To direct the xylanolytic enzyme into the secretory pathway of the host cells, a secretory signal sequence (also known as a leader sequence, prepro sequence or pre sequence) may be provided in the expression vector. The secretory signal sequence is joined to the DNA sequence encoding the xylanolytic enzyme in the correct reading frame. Secretory signal sequences are commonly positioned 5' to the DNA sequence encoding the xylanolytic enzyme. The secretory signal sequence may be that normally associated with the xylanolytic enzyme or may be from a gene encoding another secreted protein.

In a preferred embodiment, the expression vector of the invention may comprise a secretory signal sequence substantially identical to the secretory signal encoding sequence of the *Bacillus licheniformis* α-amylase gene, e.g. as described in WO 86/05812.

Also, measures for amplification of the expression may be taken, e.g. by tandem amplification techniques, involving single or double crossing-over, or by multicopy techniques, e.g. as described in U.S. Pat. No. 4,959,316 or WO 91/09129. Alternatively the expression vector may include a temperature sensitive origin of replication, e.g. as described in EP 283,075.

Procedures for ligating DNA sequences encoding the xylanolytic enzyme, the promoter and optionally the terminator and/or secretory signal sequence, respectively, and to insert them into suitable vectors containing the information necessary for replication, are well known to persons skilled in the art (cf., for instance, Sambrook et al., *Molecular Cloning. A Laboratory Manual,* Cold Spring Harbor, N.Y., 1989).

Host Cells

In yet another aspect the invention provides a host cell comprising the DNA construct of the invention and/or the recombinant expression vector of the invention.

The DNA construct of the invention may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. In this context, the term "homologous" is intended to include a cDNA sequence encoding a xylanolytic enzyme native to the host organism in question. The term "heterologous" is intended to include a DNA sequence not expressed by the host cell in nature. Thus, the DNA sequence may be from another organism, or it may be a synthetic sequence.

The host cell of the invention, into which the DNA construct or the recombinant expression vector of the invention is to be introduced, may be any cell which is capable of producing the xylanolytic enzyme and includes bacteria, yeast, fungi and higher eukaryotic cells.

Examples of bacterial host cells which, on cultivation, are capable of producing the xylanolytic enzyme of the invention are grampositive bacteria such as strains of Bacillus, in particular a strain of *B. subtilis, B. licheniformis, B. lentus, B. brevis, B. stearothermophilus, B. alkalophilus, B. amyloliquefaciens, B. coagulans, B. circulans, B. lautus, B. megatherium, B. pumilus, B. thuringiensis* or *B. agaradherens,* or strains of Streptomyces, in particular a strain of *S. lividans* or *S. murinus,* or gramnegative bacteria such as *Echerichia coli.* The transformation of the bacteria may be effected by protoplast transformation or by using competent cells in a manner known per se (cf. Sambrook et al., *Molecular Cloning. A Laboratory Manual,* Cold Spring Harbor, N.Y., 1989).

When expressing the xylanolytic enzyme in bacteria such as *E. coli,* the xylanase may be retained in the cytoplasm, typically as insoluble granules (known as inclusion bodies), or may be directed to the periplasmic space by a bacterial secretion sequence. In the former case, the cells are lysed and the granules are recovered and denatured after which the xylanolytic enzyme is refolded by diluting the denaturing agent. In the latter case, the xylanolytic enzyme may be recovered from the periplasmic space by disrupting the cells, e.g. by sonication or osmotic shock, to release the contents of the periplasmic space and recovering the xylanolytic enzyme.

Examples of suitable yeasts cells include cells of Saccharomyces spp. or Schizosaccharomyces spp., in particular strains of *Saccharomyces cerevisiae* or *Saccharomyces kluyveri*. Methods for transforming yeast cells with heterologous DNA and producing heterologous polypeptides therefrom are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the xylanolytic enzyme of the invention may be preceded by a signal sequence and optionally a leader sequence, e.g. as described above. Further examples of suitable yeast cells are strains of Kluyveromyces, such as *K. lactis,* Hansenula, e.g. *H. polymorpha,* or Pichia, e.g. *P. pastoris* (cf. Gleeson et al., *J. Gen. Microbiol.* 132, 1986, pp. 3459–3465; U.S. Pat. No. 4,882,279).

Examples of other fungal cells are cells of filamentous fungi, e.g. Aspergillus spp., Neurospora spp., Fusarium spp.

or Trichoderma spp., in particular strains of *A. oryzae*, *A. nidulans* or *A. niger*. The use of Aspergillus spp. for the expression of proteins have been described in e.g., EP 272,277 and EP 230,023. The transformation of *F. oxysporum* may, for instance, be carried out as described by Malardier et al., *Gene* 1989 78 147–156.

The transformed or transfected host cell described above is then cultured in a suitable nutrient medium under conditions permitting the expression of the xylanolytic enzyme, after which the resulting xylanolytic enzyme is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The xylanolytic enzyme produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of xylanolytic enzyme in question.

Method of Producing Xylanolytic Enzymes

In a still further aspect, the present invention provides a method of producing the xylanolytic enzyme of the invention, wherein a suitable host cell, which has been transformed with a DNA sequence encoding the xylanolytic enzyme, is cultured under conditions permitting the production of the enzyme, and the resulting enzyme is recovered from the culture.

The medium used to culture the transformed host cells may be any conventional medium suitable for growing the host cells in question. The expressed xylanolytic enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Enzyme Preparations

In a still further aspect, the present invention provides an enzyme preparation comprising a xylanolytic enzyme, which enzyme, (a) is encoded by a DNA construct according to any of claims 1–7; or (b) produced by the method according to claim 12, and/or (c) is immunologically reactive with an antibody raised against a purified xylanolytic enzyme derived from the strain *Bacillus agaradherens*, NCIMB 40482.

The enzyme preparation of the invention may be one which comprises an enzyme of the invention as the major enzymatic component, and may in particular be a monocomponent enzyme preparation.

The enzyme preparation may be prepared in accordance with methods known in the art and may be in the form of a liquid or a dry preparation. For instance, the enzyme preparation may be in the form of a granulate or a micro granulate. The enzyme preparation may be stabilized in accordance with methods known in the art.

Examples are given below of preferred uses of the enzyme preparation of the invention. The dosage of the enzyme preparation of the invention and other conditions under which the preparation is used may be determined on the basis of methods known in the art.

Industrial Applications

The enzyme preparation according to the invention may be applied in industrial processes conventionally involving the action of xylanolytic enzymes. Major applications for xylanolytic enzymes are enzymatic breakdown of agricultural wastes for production of alcohol fuels, enzymatic treatment of animal feeds to release free pentose sugars, manufacturing of dissolving pulps yielding cellulose, and bio-bleaching of wood pulp.

In a preferred embodiment the enzyme preparation of the invention may be used for the treatment of lignocellulosic materials, in particular paper and pulp, or as an animal feed additive.

The invention is described in further detail in the following examples which are not in any way intended to limit the scope of the invention as claimed.

EXAMPLES

The invention is further illustrated with reference to the following examples which are not intended to be in any way limiting to the scope of the invention as claimed.

MATERIALS AND METHODS

Identification of Xylanolytic Activity

The xylanolytic activity may be measured in endo-xylanase units (EXU), determined at pH 9.0 with remazol-xylan as substrate.

A xylanase sample is incubated with remazol-xylan substrate. The background of non-degraded dyed substrate is precipitated by ethanol. The remaining blue colour in the supernatant is proportional to the xylanase activity, and the xylanase units are then determined relatively to an enzyme standard at standard reaction conditions, i.e. at 50.0+/−0.1° C., pH 9.0, and 30 minutes reaction time.

A folder AF 293.9/1 describing this analytical method in more detail is available upon request to Novo Nordisk A/S, Denmark, which folder is hereby included by reference.

Hybridization Conditions

Suitable hybridization conditions for determining hybridization between an oligonucleotide probe and an "analogous" DNA sequence of the invention may be defined as either low to medium stringency conditions or high stringency conditions.

Low to Medium Stringency

A filter containing the DNA fragments to hybridize is subjected to presoaking in 5x SSC, and prehydbridized for 1 hour at about 40° C. in a solution of 20% formamide, 5x Denhardt's solution, 50 mM sodium phosphate, pH 6.8, and 50 $\mu$g of denatured sonicated calf thymus DNA. After hybridization in the same solution supplemented with 100 $\mu$M ATP for 18 hours at about 40° C., the product is washed three times in 2x SSC at a temperature of about 45° C. for 30 minutes.

Molecules to which the oligonucleotide probe hybridizes under these conditions are detected using standard detection procedures (e.g. Southern blotting).

High Stingency Hybridization

A filter containing the DNA fragments to hybridize is subjected to presoaking in 5x SSC, and prehybridized for 1 hour at about 50° C. in a solution of 5x SSC, 5x Denhardt's solution, 50 mM sodium phosphate, pH 6.8, and 50 µg of denatured sonicated calf thymus DNA. After hybridization in the same solution supplemented with 50 µCi 32-P-dCTP labelled probe for 18 hours at ~50° C., the product is washed three times in 2x SSC, 0.2% SDS at 50° C. for 30 minutes.

Molecules to which the oligonucleotide probe hybridizes under these conditions are detected using a x-ray film.

A suitable oligonucleotide probe to be used in the hybridization may be prepared on the basis of the DNA sequence shown in SEQ ID NO: 1, or any sub-sequence thereof.

Immunological Cross-Reactivity

Antibodies useful for determining immunological cross-reactivity are prepared using a purified xylanolytic enzyme obtained from the strain NCIMB 40482. More specifically, antiserum against the xylanolytic enzyme of the invention are raised by immunizing rabbits (or other rodents) according to the procedure described by Axelsen N H, et al. in "A Manual of Quantitative Immunoelectrophoresis", Blackwell Scientific Publications, 1973, Chapter 23, or by Johnstone A & Thorpe R in "Immunochemistry in Practice" , Blackwell Scientific Publications, 1982 (more specifically p. 27–31).

Purified immunoglobulins may be obtained from the antisera, for example by salt precipitation (($NH_4$)$_2SO_4$), followed by dialysis and ion exchange chromatography, e.g. on DEAE-Sephadex. Immunochemical characterization of proteins may be done either by Ouchterlony double-diffusion analysis [Ouchterlony O, in "Handbook of Experimental Immunology", Weir D M, Ed., Blackwell Scientific Publications, 1967, pp. 655–706], by crossed immunoelectrophoresis [Axelsen N H, et al., supra, Chapters 3 and 4], or by rocket immunoelectrophoresis [Axelsen N H, et al., supra, Chapter 2].

EXAMPLE 1

Cloning of the XynA Gene from *Bacillus agaradherens*

Chromosomal DNA was isolated from the strain NCIMB 40482 by standard procedures, and cut partially by Sau3A. The *E. coli* plasmid SJ1678 (cf. FIG. 1), which has been described in WO 94/19454, was cut by BamHI. The larger fragment was isolated, and after ligation to the *Bacillus agaradherens* DNA, a genebank was constructed in a *E. coli* strain by selecting for chloramphenicol resistance.

The genebank was screened for xylanolytic activity on dyed xylan containing media. A xylan positive colony PL2354, containing the XynA gene encoding the xylanase in a approx. 3,8 Kb insert, was selected, and by sequencing the 5'-end of the cDNA plasmid using the chain-termination method (Sanger F, Nicklen S and Coulson A R, *Proc. Natl. Acad. Sci.* U.S.A. 1977 74 5463–5467) and the Sequenase® system (United States Biochemical), the XynA gene was DNA sequenced. The sequence is presented as SEQ ID NO: 1.

We claim:

1. A DNA construct comprising a DNA sequence encoding a xylanolytic enzyme, wherein the DNA sequence comprises
   a) the sequence of SEQ ID NO: 1; or
   b) a DNA sequence which
      (i) hybridizes with the DNA sequence of SEQ ID NO: 1 under conditions of high stringency;
      (ii) has at least 95% homology to the sequence of SEQ ID NO:1.

2. The DNA construct of claim 1, wherein the construct is derived from a strain of Bacillus agaradherens.

3. The DNA construct of claim 2, wherein the construct is derived from Bacillus agaradherens, DSM 8721.

4. The DNA construct of claim 2, wherein the construct is derived from Bacillus agaradherens, NCIMB 40482.

5. The DNA construct of claim 1, further comprising a nucleotide sequence encoding a promoter of the Bacillus stearothermophilus maltogenic amylase gene, the Bacillus licheniformis µ-amylase gene, the Bacillus amyloliquefaciens BAN amylase gene, the Bacillus subtilis alkaline protease gene, the Bacillus pumilus xylanase or the Bacillus pumilus xylosidase gene.

6. A recombinant expression vector comprising the DNA construct of claim 1.

7. A cell comprising the DNA construct of claim 1.

8. A cell comprising the expression vector of claim 6.

9. The cell of claim 8, wherein the cell is a procaryotic cell.

10. The cell of claim 9, wherein the procaryotic cell is a Bacillus strain.

11. The cell of claim 10, wherein the cell is B. subtilis, B. licheniformis, B. lentus, B. brevis, B. stearothermophilus, B. alkalophilus, B. amyloliquefaciens, B. coagulans, B. circulans, B. lautus, B. megatherium, B. pumilus, B. thuringiensis or B. agaradherens.

12. A method of producing a xylanolytic enzyme, comprising culturing the cell of claim 8 under conditions permitting the production of the enzyme, and recovering the enzyme from the culture.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 871 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus agaradherens
        ( B ) STRAIN: NCIMB 40482

( i x ) FEATURE:
        ( A ) NAME/KEY: CDS
        ( B ) LOCATION:82..744

( x i ) SEQUENCE DESCRIPTION: SEQ ID NO: 1:

```
ATGAGACAAA  AGAAATTGAC  GTTCATTTTA  GCCTTTTTAG  TTTGTTTTGC  ACTAACCTTA                60

CCTGCAGAAA  TAATTCAGGC  A CAA  ATC  GTC  ACC  GAC  AAT  TCC  ATT  GGC  AAC           111
                         Gln  Ile  Val  Thr  Asp  Asn  Ser  Ile  Gly  Asn
                          1              5                        10

CAC  GAT  GGC  TAT  GAT  TAT  GAA  TTT  TGG  AAA  GAT  AGC  GGT  GGC  TCT  GGG      159
His  Asp  Gly  Tyr  Asp  Tyr  Glu  Phe  Trp  Lys  Asp  Ser  Gly  Gly  Ser  Gly
               15                        20                       25

ACA  ATG  ATT  CTC  AAT  CAT  GGC  GGT  ACG  TTC  AGT  GCC  CAA  TGG  AAC  AAT      207
Thr  Met  Ile  Leu  Asn  His  Gly  Gly  Thr  Phe  Ser  Ala  Gln  Trp  Asn  Asn
               30                        35                       40
```

| | | | | | | | | | | | | | | | | |
|---|---|---|---|---|---|---|---|---|---|---|---|---|---|---|---|---|
| GTT | AAC | AAC | ATA | TTA | TTC | CGT | AAA | GGT | AAA | AAA | TTC | AAT | GAA | ACA | CAA | 255 |
| Val | Asn | Asn | Ile | Leu | Phe | Arg | Lys | Gly | Lys | Lys | Phe | Asn | Glu | Thr | Gln | |
| | | 45 | | | | | 50 | | | | | 55 | | | | |
| ACA | CAC | CAA | CAA | GTT | GGT | AAC | ATG | TCC | ATA | AAC | TAT | GGC | GCA | AAC | TTC | 303 |
| Thr | His | Gln | Gln | Val | Gly | Asn | Met | Ser | Ile | Asn | Tyr | Gly | Ala | Asn | Phe | |
| | 60 | | | | | 65 | | | | | 70 | | | | | |
| CAG | CCA | AAC | GGA | AAT | GCG | TAT | TTA | TGC | GTC | TAT | GGT | TGG | ACT | GTT | GAC | 351 |
| Gln | Pro | Asn | Gly | Asn | Ala | Tyr | Leu | Cys | Val | Tyr | Gly | Trp | Thr | Val | Asp | |
| 75 | | | | | 80 | | | | | 85 | | | | | 90 | |
| CCT | CTT | GTC | GAA | TAT | TAT | ATT | GTC | GAT | AGT | TGG | GGC | AAC | TGG | CGT | CCA | 399 |
| Pro | Leu | Val | Glu | Tyr | Tyr | Ile | Val | Asp | Ser | Trp | Gly | Asn | Trp | Arg | Pro | |
| | | | | 95 | | | | | 100 | | | | | 105 | | |
| CCA | GGG | GCA | ACG | CCT | AAG | GGA | ACC | ATC | ACT | GTT | GAT | GGA | GGA | ACA | TAT | 447 |
| Pro | Gly | Ala | Thr | Pro | Lys | Gly | Thr | Ile | Thr | Val | Asp | Gly | Gly | Thr | Tyr | |
| | | | 110 | | | | 115 | | | | | | 120 | | | |
| GAT | ATC | TAT | GAA | ACT | CTT | AGA | GTC | AAT | CAG | CCC | TCC | ATT | AAG | GGG | ATT | 495 |
| Asp | Ile | Tyr | Glu | Thr | Leu | Arg | Val | Asn | Gln | Pro | Ser | Ile | Lys | Gly | Ile | |
| | | 125 | | | | | 130 | | | | | 135 | | | | |
| GCC | ACA | TTT | AAA | CAA | TAT | TGG | AGT | GTC | CGA | AGA | TCG | AAA | CGC | ACG | AGT | 543 |
| Ala | Thr | Phe | Lys | Gln | Tyr | Trp | Ser | Val | Arg | Arg | Ser | Lys | Arg | Thr | Ser | |
| | 140 | | | | | 145 | | | | | 150 | | | | | |
| GGC | ACA | ATT | TCT | GTC | AGC | AAC | CAC | TTT | AGA | GCG | TGG | GAA | AAC | TTA | GGG | 591 |
| Gly | Thr | Ile | Ser | Val | Ser | Asn | His | Phe | Arg | Ala | Trp | Glu | Asn | Leu | Gly | |
| 155 | | | | | 160 | | | | | 165 | | | | | 170 | |
| ATG | AAC | ATG | GGG | AAA | ATG | TAT | GAA | GTC | GCG | CTT | ACT | GTA | GAA | GGC | TAT | 639 |
| Met | Asn | Met | Gly | Lys | Met | Tyr | Glu | Val | Ala | Leu | Thr | Val | Glu | Gly | Tyr | |
| | | | | 175 | | | | | 180 | | | | | 185 | | |
| CAA | AGT | AGC | GGA | AGT | GCT | AAT | GTA | TAT | AGC | AAT | ACA | CTA | AGA | ATT | AAC | 687 |
| Gln | Ser | Ser | Gly | Ser | Ala | Asn | Val | Tyr | Ser | Asn | Thr | Leu | Arg | Ile | Asn | |
| | | | 190 | | | | | 195 | | | | | 200 | | | |
| GGT | AAC | CCT | CTC | TCA | ACT | ATT | AGT | AAT | GAC | AAG | AGC | ATA | ACT | CTA | GAT | 735 |
| Gly | Asn | Pro | Leu | Ser | Thr | Ile | Ser | Asn | Asp | Lys | Ser | Ile | Thr | Leu | Asp | |
| | | 205 | | | | | 210 | | | | | 215 | | | | |
| AAA | AAC | AAT | TAAAAATCCT | TATCTCTTTC | GGTTCAGTTC | TCATTATTTT | | | | | | | | | | 784 |
| Lys | Asn | Asn | | | | | | | | | | | | | | |
| | | 220 | | | | | | | | | | | | | | |

CAAATAACCT CCCGGTTGGA TCTTTTCCAA CGGGAGGTTT TATTGGAAAG GTTAAGTATA 844

GTATACTCCG ATTCCATCCA GAGGAAT 871

( 2 ) INFORMATION FOR SEQ ID NO: 2:

( i ) SEQUENCE CHARACTERISTICS:
        ( A ) LENGTH: 221 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

| | | | | | | | | | | | | | | |
|---|---|---|---|---|---|---|---|---|---|---|---|---|---|---|
| Gln | Ile | Val | Thr | Asp | Asn | Ser | Ile | Gly | Asn | His | Asp | Gly | Tyr | Asp | Tyr |
| 1 | | | | 5 | | | | | 10 | | | | | 15 | |
| Glu | Phe | Trp | Lys | Asp | Ser | Gly | Gly | Ser | Gly | Thr | Met | Ile | Leu | Asn | His |
| | | | 20 | | | | | 25 | | | | | 30 | | |
| Gly | Gly | Thr | Phe | Ser | Ala | Gln | Trp | Asn | Asn | Val | Asn | Asn | Ile | Leu | Phe |
| | | 35 | | | | | 40 | | | | | 45 | | | |
| Arg | Lys | Gly | Lys | Lys | Phe | Asn | Glu | Thr | Gln | Thr | His | Gln | Gln | Val | Gly |
| | 50 | | | | | 55 | | | | | 60 | | | | |
| Asn | Met | Ser | Ile | Asn | Tyr | Gly | Ala | Asn | Phe | Gln | Pro | Asn | Gly | Asn | Ala |
| 65 | | | | | 70 | | | | | 75 | | | | | 80 |

```
Tyr Leu Cys Val Tyr Gly Trp Thr Val Asp Pro Leu Val Glu Tyr Tyr
             85                  90                    95

Ile Val Asp Ser Trp Gly Asn Trp Arg Pro Pro Gly Ala Thr Pro Lys
            100                 105                110

Gly Thr Ile Thr Val Asp Gly Gly Thr Tyr Asp Ile Tyr Glu Thr Leu
        115                 120                125

Arg Val Asn Gln Pro Ser Ile Lys Gly Ile Ala Thr Phe Lys Gln Tyr
    130                 135                 140

Trp Ser Val Arg Arg Ser Lys Arg Thr Ser Gly Thr Ile Ser Val Ser
145                 150                 155                 160

Asn His Phe Arg Ala Trp Glu Asn Leu Gly Met Asn Met Gly Lys Met
            165                 170                 175

Tyr Glu Val Ala Leu Thr Val Glu Gly Tyr Gln Ser Ser Gly Ser Ala
            180                 185                 190

Asn Val Tyr Ser Asn Thr Leu Arg Ile Asn Gly Asn Pro Leu Ser Thr
        195                 200                 205

Ile Ser Asn Asp Lys Ser Ile Thr Leu Asp Lys Asn Asn
    210                 215                 220
```